(12) United States Patent
Niewöhner et al.

(10) Patent No.: US 6,777,416 B2
(45) Date of Patent: Aug. 17, 2004

(54) ISOXAZOLO PYRIMIDINONES AND THE USE THEREOF

(75) Inventors: Ulrich Niewöhner, Wermelskirchen (DE); Helmut Haning, Milford, CT (US); Thomas Lampe, Wuppertal (DE); Mazen Es-Sayed, Langenfeld (DE); Gunter Schmidt, Wuppertal (DE); Erwin Bischoff, Wuppertal (DE); Klaus Dembowsky, Boston, MA (US); Elisabeth Perzborn, Wuppertal (DE); Karl-Heinz Schlemmer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,659

(22) PCT Filed: Dec. 12, 2000

(86) PCT No.: PCT/EP00/12562

§ 371 (c)(1),
(2), (4) Date: Oct. 22, 2002

(87) PCT Pub. No.: WO01/47934

PCT Pub. Date: Jul. 5, 2001

(65) Prior Publication Data

US 2003/0149033 A1 Aug. 7, 2003

(30) Foreign Application Priority Data

Dec. 24, 1999 (DE) .......................... 199 62 925
Jan. 27, 2000 (DE) .......................... 100 03 287

(51) Int. Cl.[7] .................... A61K 31/519; C07D 498/04
(52) U.S. Cl. .................... 514/252.16; 514/252.02; 514/260.1; 544/238; 544/255
(58) Field of Search ................ 544/255, 238; 514/252.02, 252.16, 260.1

(56) References Cited

U.S. PATENT DOCUMENTS

| | | | |
|---|---|---|---|
| 4,666,908 A | 5/1987 | Hamilton | 514/229 |
| 5,250,534 A | 10/1993 | Bell et al. | 514/258 |
| 5,525,604 A | 6/1996 | Lee et al. | 514/256 |
| 5,656,629 A | 8/1997 | Bacon et al. | 514/234.5 |
| 6,362,178 B1 | 3/2002 | Niewohner et al. | 514/218 |

FOREIGN PATENT DOCUMENTS

| | | |
|---|---|---|
| DE | 19838705 | 3/2000 |
| EP | 0463756 | 2/1992 |
| EP | 0911333 | 4/1999 |
| WO | 9719947 | 5/1997 |

OTHER PUBLICATIONS

Laurent, S., Barbieux–Flammang, M., Haverbeke, Y. V., Flammang, R., and Wentrup, C., "Synthesis of Isoxazolo[4,5–d]Pyridiminones, and Their Isomerization into Oxazolo [4,5–d]Pyrimidinones on Flash Vacuum Pyrolysis", Bull. Soc. Chim. Belg., 103(5–6): 181–184 (1994).

Desimoni, G., and Grunanger, P., "Sull'acido 3–fenil–4–ammino–5–isossazolcarbossilico", Gazz. Chim. Ital., 97(1):25–33 (1967).

Xia, Y., Chackalamannil, S., Czarniecki, M., Tsai, H., Vaccaro, H., Cleven, R., Cook, J., Fawzi, A., Watkins, R., and Zhang, H., "Synthesis and Evaluation of Polycyclic Pyrazolo[3,4–d]pyrimidines as PDEI and PDE5 cGMP Phosphodiesterase Inhibitors", J. Med. Chem., 40: 4372–4377 (1997).

Beavo, J., Reifsnyder, D., "Primary Sequence of Cyclic Nucleotide Phosphodiesterase Isozymes and the Design of Selective Inhibitors", TIPS Reviews, 11: 150–155 (Apr. 1990).

Stoclet, J., Keravis, T., Komas, N., Lugnier, C., "Cyclic Nucleotide Phosphodiesterases as Therapeutic Targets in Cardiovascular Diseases", Exp. Opin. Invest. Drugs,4: 1081–1100 (1995).

*Primary Examiner*—Richard L. Raymond
(74) *Attorney, Agent, or Firm*—Susan M. Pellegrino

(57) ABSTRACT

The invention relates to novel isoxazolo pyrimidinones of general formula (I), a method for producing the same and the pharmaceutical use thereof.

9 Claims, No Drawings

ISOXAZOLO PYRIMIDINONES AND THE USE THEREOF

This is a 371 of PCT/EP00/12562, filed on Dec. 12, 2000.

The present invention relates to novel isoxazolopyrimidinones, to processes for preparing them and to their use as medicaments, in particular as inhibitors of cGMP-metabolizing phosphodiesterases.

The publication Bull. Soc. Chim. Belg. (1994), 103 (5-6), 181-4 describes the synthesis of isoxazolo[4,5-d] pyrimidinones which are unsubstituted in the 5 position. Compounds possessing a phenyl radical or substituted phenyl radical in the 5 position are not described. There is no report of the described substances having a biological effect, in particular being able to inhibit phosphodiesterases.

The compounds according to the invention are potent inhibitors of cyclic guanosine 3',5'-monophophate-metabolizing phosphodiesterases (cGMP-PDEs). In accordance with the nomenclature of Beavo and Reifsnyder (Trends in Pharmacol. Sci. 11, 150–155, 1990), these phosphodiesterases are the phosphodiesterase isoenzymes PDE-I, PDE-II and PDE-V.

An increase in the concentration of cGMP can lead to therapeutic, antiaggregatory, antithrombotic, antiproliferative, antivasospastic, vasodilatory, natriuretic and diuretic effects. It can exert an effect on the short-term or long-term modulation of vascular and cardiac inotropy, cardiac rhythm and stimulus conduction in the heart (J. C. Stoclet, T. Keravis, N. Komas and C. Kugnier, Exp. Opin. Invest. Drugs (1995), 4 (11), 1081–1100). Inhibition of the cGMP-PDEs can also strengthen erection. These compounds are therefore suitable for treating erectile dysfunction.

The present invention now relates to novel isoxazolidinones of the general formula (I)

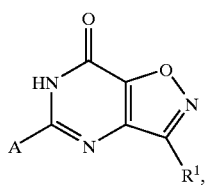

(I)

in which $R^1$ represents $(C_3-C_8)$-cycloalkyl or represents straight-chain or branched alkyl having up to 4 carbon atoms, A represents radicals of the formulae

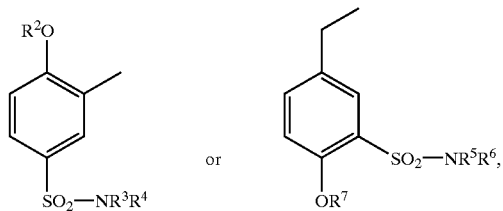

in which $R^2$ and $R^7$ are identical or different and denote hydrogen or straight-chain or branched alkyl having up to 4 carbon atoms, $R^3$, $R^4$, $R^5$ and $R^6$ are identical or different and denote hydrogen, a 5- to 6-membered aromatic heterocycle having up to 3 heteroatoms from the series S, N and/or O or aryl having from 6 to 10 carbon atoms, where the ring systems are optionally substituted, up to three times, identically or differently, by hydroxyl, halogen, $(C_1-C_5)$-alkyl or $(C_1-C_6)$-alkoxy, or $R^3$, $R^4$, $R^5$ and $R^6$ are identical or different and denote $(C_1-C_6)$-alkyl which is optionally substituted by aryl having from 6 to 10 carbon atoms and can, for its part, be substituted, up to 3 times, identically or differently, by $(C_1-C_6)$-alkyl, $(C_1-C_6)$-alkoxy, hydroxyl or halogen, or $R^3$ and $R^4$ and/or $R^5$ and $R^6$, together with the nitrogen atom to which they are bonded, form radicals of the formulae

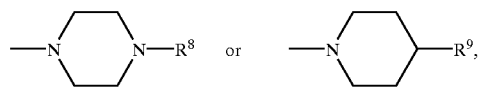

where $R^8$ denotes hydrogen or $(C_1-C_6)$-alkyl, which is optionally substituted by hydroxyl, and $R^9$ denotes hydrogen or hydroxyl, and the salts, N-oxides and isomeric forms thereof.

The compounds according to the invention can exist in stereoisomeric forms which either relate to each other as image and mirror image (enantiomers) or which do not relate to each other as image and mirror image (diastereomers). The invention relates to both the enantiomers or diastereomers or their respective mixtures. The racemic forms, as well as the diastereomers, can be separated into the stereoisomerically uniform constituents in a known manner.

The substances according to the invention can also be present as salts. Within the context of the invention, preference is given to physiologically harmless salts.

Physiologically harmless salts can be salts of the compounds according to the invention with inorganic or organic acids. Preference is given to salts with inorganic acids, such as, for example, hydrochloric acid, hydrobromic acid, phosphoric acid or sulfuric acid, or salts with organic carboxylic or sulfonic acids, such as, for example, acetic acid, maleic acid, fumaric acid, malic acid, citric acid, tartaric acid, lactic acid or benzoic acid, or methanesulfonic acid, ethanesulfonic acid, phenylsulfonic acid, toluenesulfonic acid or naphthalenedisulfonic acid.

Physiologically harmless salts can equally well be metal or ammonium salts of the compounds according to the invention. Particular preference is given, for example, to sodium, potassium, magnesium or calcium salts, and also to ammonium salts which are derived from ammonia, or to organic amines, such as, for example, ethylamine, di- or triethylamine, di- or triethanolamine, dicyclohexylamine, dimethylaminoethanol, arginine, lysine, ethylenediamine or 2-phenylethylamine.

$(C_3-C_8)$-Cycloalkyl represents cyclopropyl, cyclopentyl, cyclobutyl, cyclohexyl, cycloheptyl or cyclooctyl. Those which may be mentioned as being preferred are: cyclopropyl, cyclopentyl and cyclohexyl.

$(C_6-C_{10})$-Aryl represents an aromatic radical having from 6 to 10 carbon atoms. Preferred aryl radicals are phenyl and naphthyl.

$(C_1-C_6)$-Alkyl represents a straight-chain or branched alkyl radical having from 1 to 6 carbon atoms. Those which may be mentioned by way of example are: methyl, ethyl, n-propyl, isopropyl, n-butyl, isobutyl, tert-butyl, n-pentyl and n-hexyl. Preference is given to a straight-chain or branched branched alkyl radical having from 1 to 4 carbon atoms. Particular preference is given to a straight-chain or branched alkyl radical having from 1 to 3 carbon atoms.

$(C_1–C_6)$-Alkoxy represents a straight-chain or branched alkoxy radical having 1 to 6 carbon atoms. Those which may be mentioned by way of example are: methoxy, ethoxy, n-propoxy, isopropoxy, n-butoxy, isobutoxy, tert-butoxy, n-pentoxy and n-hexoxy. Preference is given to a straight-chain or branched alkoxy radical having from 1 to 4 carbon atoms. Particular preference is given to a straight-chain or branched alkoxy radical having from 1 to 3 carbon atoms.

Halogen generally represents fluorine, chlorine, bromine and iodine. Preference is given to fluorine, chlorine and bromine. Particular preference is given to fluorine and chlorine.

A 5- to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Preference is given to pyridyl, pyrimidyl, pyridazinyl, furyl and thienyl.

Preference is given to compounds according to the invention of the general formula (I),
in which
$R^1$ represents $(C_3–C_6)$-cycloalkyl or represents n-propyl,
A represents radicals of the formulae

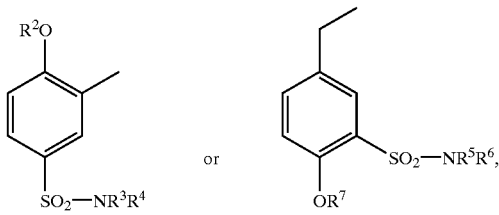

in which
$R^2$ and $R^7$ are identical or different and denote hydrogen, methyl or ethyl,
$R^3$, $R^4$, $R^5$ and $R^6$ are identical or different and denote hydrogen, pyridyl, pyrimidyl, pyridazinyl, furyl, imidazolyl, thienyl, pyrryl or phenyl, where the ring systems are optionally substituted, up to 2 times, identically or differently, by hydroxyl, fluorine, chlorine, $(C_1–C_4)$-alkyl or $(C_1–C_4)$-alkoxy, or
$R^3$, $R^4$, $R^5$ and $R^6$ are identical or different and denote $(C_1–C_4)$-alkyl which is optionally substituted by phenyl which, for its part, can be substituted, up to 2 times, identically or differently, by $(C_1–C_4)$-alkoxy, fluorine or chlorine, or
$R^3$ and $R^4$ and/or $R^5$ and $R^6$, together with the nitrogen atom to which they are bonded, form radicals of the formulae

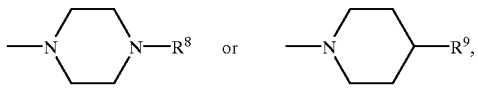

where
$R^8$ denotes hydrogen or $(C_1–C_6)$-alkyl which is optionally substituted by hydroxyl, and
$R^9$ denotes hydroxyl,
and the salts, N-oxides and isomeric forms thereof.

Particular preference is given to compounds according to the invention of the general formula (I), in which
$R^1$ represents cyclopentyl or n-propyl,
A represents radicals of the formulae

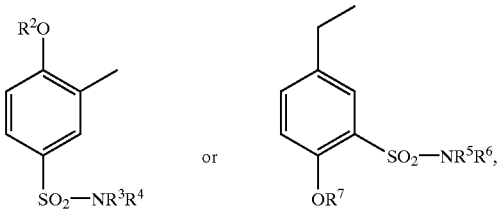

in which
$R^2$ and $R^7$ are identical or different and denote methyl or ethyl,
$R^3$, $R^4$, $R^5$ and $R^6$ are identical or different and denote hydrogen, pyridyl or phenyl, where the ring systems are optionally substituted, up to 2 times, identically or differently, by fluorine, methoxy or ethoxy, or
$R^3$, $R^4$, $R^5$ and $R^6$ are identical or different and denote $(C_1–C_3)$-alkyl which is optionally substituted by phenyl which, for its part, is substituted, up to 2 times, identically or differently, by methoxy or ethoxy, or
$R^3$ and $R^4$ and/or $R^5$ and $R^6$, together with the nitrogen atom, form radicals of the formulae

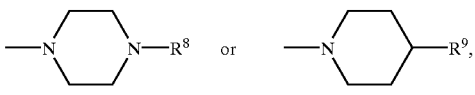

where
$R^8$ denotes hydrogen or $(C_1–C_3)$-alkyl or a radical of the formula $—(CH_2)_2—OH$, and
$R^9$ denotes hydroxyl,
and the salts, N-oxides and isomeric forms thereof.

Very particular preference is given to the following compounds:

| Structure |
| --- |
| 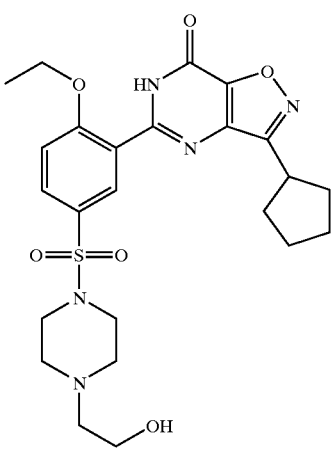 |

-continued

Structure

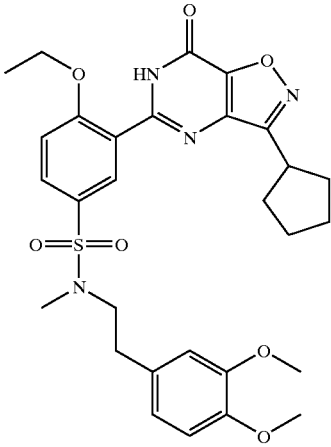

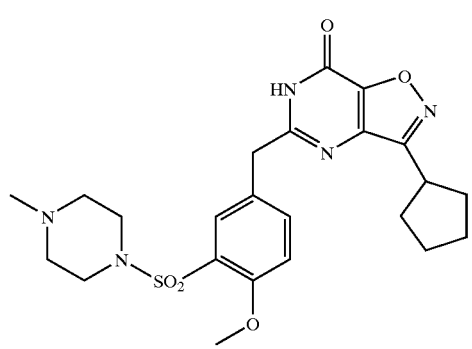

In addition, a process for preparing the compounds according to the invention of the general formula (I) was found, which process is characterized in that compounds of the general formula (II)

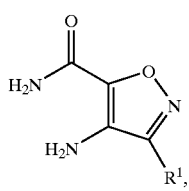
(II)

in which

R¹ has the abovementioned meaning, are initially converted, by reaction with compounds of the general formula (III)

A'—CO—Cl  (III), in which

A' represents radicals of the formulae

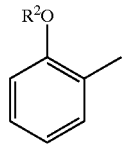 or 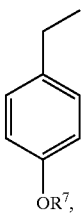, in which

R² and R⁷ have the abovementioned meaning,
in inert solvents, where appropriate in the presence of a base, into the compounds of the general formula (IV)

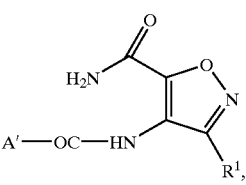
(IV)

in which

A' and R¹ have the abovementioned meaning,
a cyclization is subsequently carried out, in the presence of POCl₃ or of alkali metal hydroxide or alkaline earth metal hydroxide, to give the compounds of the general formula (V)

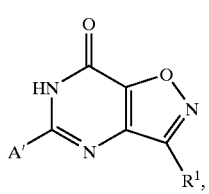
(V)

in which

A' and R¹ have the abovementioned meaning,
and, in a further step, the compounds of the general formula (VI)

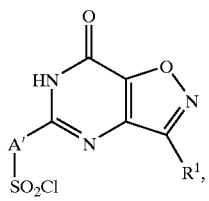
(VI)

in which

A' and R¹ have the abovementioned meaning,
are prepared by reaction with ClSO₃H,
and, finally, are reacted with amines of the general formula (VII)

HNR¹⁰R¹¹  (VII), in which

R[10] and R[11] encompass the abovementioned scope of meaning of R[3], R[4], R[5] and R[6].

The process according to the invention can be explained, by way of example, by means of the following formula schemes:

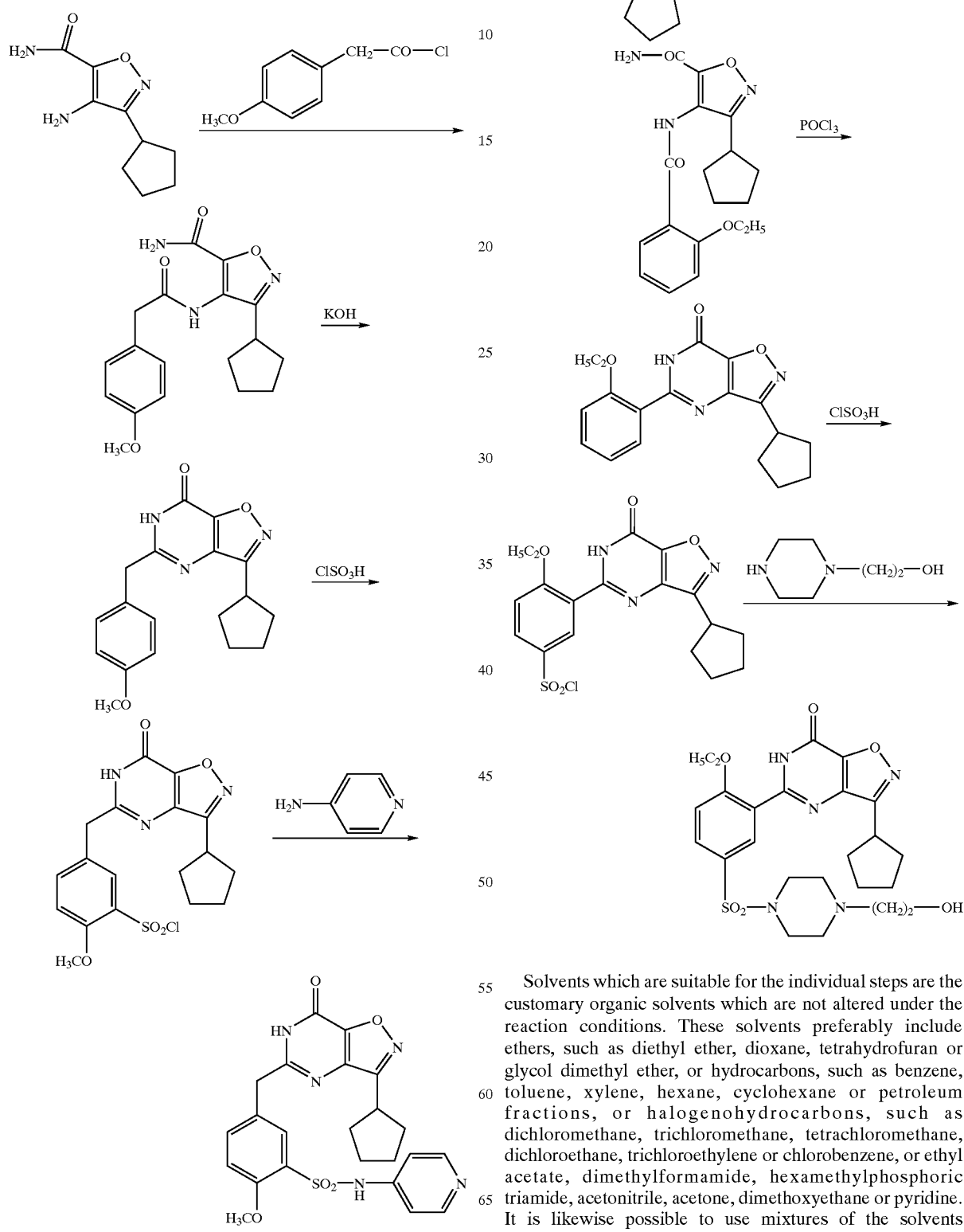

Solvents which are suitable for the individual steps are the customary organic solvents which are not altered under the reaction conditions. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethane, trichloroethylene or chlorobenzene, or ethyl acetate, dimethylformamide, hexamethylphosphoric triamide, acetonitrile, acetone, dimethoxyethane or pyridine. It is likewise possible to use mixtures of the solvents mentioned.

In general, the reaction temperatures can vary over a relatively wide range. In general, the temperatures employed are in a range of from −20° C. to 200° C., preferably of from 0° C. to 70° C.

In general, the process steps according to the invention are carried out under standard pressure. However, it is also possible to carry them out under positive pressure or under negative pressure (e.g. in a range from 0.5 to 5 bar).

The reactions can, for example, take place in a temperature range of from 0° C. to room temperature and under standard pressure.

The compounds of the general formula (II) are novel and can be prepared (e.g. by analogy with Gazz. Chim. Ital., 97, 1967, 25–33) by converting compounds of the general formula (VII)

R¹—CHO                    (VII), in which

R¹ has the abovementioned meaning, by reaction in the system 1.) CH₃—NO₂/KF and 2.) K₂Cr₂O₄, into the compounds of the general formula (VIII)

R¹—CO—CH₂—NO₂             (VIII), in which

R¹ has the abovementioned meaning, subsequently preparing the compounds of the general formula (IX)

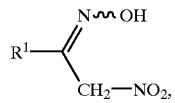

in which

R¹ has the abovementioned meaning, by reaction with hydroxylamine, cyclizing these compounds with ethyl oxalyl chloride, in a solvent (e.g. ether), to give the compounds of the general formula (X)

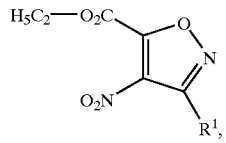

in which

R¹ has the abovementioned meaning, converting these compounds, by the action of ammonia, into the compounds of the general formula (XI)

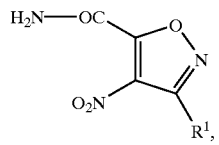

in which

R¹ has the abovementioned meaning, and, in a last step, reducing these compounds with Zn/NH₄Cl to give the compounds of the general formula (II).

The compounds of the general formula (III) are known.
The compounds of the general formula (IV) are not known.
The compounds of the general formula (V) are not known.
The compounds of the general formula (VI) are not known.
The compounds of the general formula (VII) are known.
The compounds of the general formula (VIII) are known.
The compounds of the general formula (IX) are known.
The compounds of the general formula (X) are known.
The compounds of the general formula (XI) are known.

The compounds according to the invention of the general formula (I) exhibit a valuable pharmacological spectrum of activity which it was not possible to foresee.

They inhibit either one or several of the c-GMP-metabolizing phosphodiesterases (PDE I, PDE II and PDE V). This leads to an increase in c-GMP. The differing expression of the phosphodiesterases in different cells, tissues and organs, as well as the differing subcellular location of these enzymes, make it possible, in combination with the selective inhibitors according to the invention, to address the different cGMP-regulated processes selectively.

In addition, the compounds according to the invention augment the effect of substances such as, for example, EDRF (endothelium-derived relaxing factor) and ANP (atrial natriuretic peptide), of nitro vasodilators and all other substances which increase the concentration of cGMP in another way than phosphodiesterase inhibitors.

The compounds according to the invention of the general formula (I) are therefore suitable for the prophylaxis and/or treatment of diseases in which an increase in the concentration of cGMP is therapeutic, i.e. diseases which are connected with cGMP-regulated processes (usually simply termed "cGMP-related diseases"). These diseases include cardiovascular diseases, diseases of the urogenital system and cerebrovascular diseases.

Within the meaning of the present invention, the term "cardiovascular diseases" covers diseases such as, for example, high blood pressure, neuronal hypertension, stable and unstable angina, peripheral and cardiac vascular diseases, arrhythmias, thromboembolic diseases and ischemias such as myocardial infarction, stroke, transistory and ischemic attacks, angina pectoris, peripheral circulatory disturbances, prevention of restenoses following thrombolysis therapy, percutaneous transluminal angioplasty (PTA), percutaneous transluminal coronary angioplasties (PTCA) and bypass.

Furthermore, the compounds according to the invention of the general formula (I) can also have importance for cerebrovascular diseases. These include, for example, cerebral ischemia, stroke, reperfusion damage, brain trauma, edemas, cerebral thrombosis, dementia and Alzheimer's disease.

The relaxing effect on smooth musculature makes them suitable for treating disorders of the urogenital system such as prostate hypertrophy and incontinence and also, in particular, for treating erectile dysfunction and female sexual dysfunction.

Activity of the Phosphordiesterases (PDEs)

The cGMP-stimulatable PDE II, the cGMP-inhibitable PDE III and the cAMP-specific PDE IV were isolated either from porcine heart myocardium or from bovine heart myocardium. The Ca⁺-calmodulin-stimulatable PDE I was isolated from porcine aorta, porcine brain or, preferably, from bovine aorta. The c-GMP-specific PDE V was obtained from porcine small intestine, porcine aorta, human blood platelets and, preferably, from bovine aorta. Purification was effected by means of anion exchange chromatography on Pharmacia MonoQ$^R$, essentially in accordance with the method described by M. Hoey and Miles D. Houslay, Biochemical Pharmacology, Vol. 40, 193–202 (1990) and C. Lugman et al., Biochemical Pharmacology, Vol. 35, 1743–1751 (1986).

The enzyme activity is determined in a 100 μl test formulation, in 20 mM Tris/HCl buffer pH 7.5, which contains 5 mM MgCl$_2$, 0.1 mg/ml bovine serum albumin and either 800 Bq of $^3$HcAMP or $^3$HcGMP. The final concentration of the corresponding nucleotides is $10^{-6}$ mol/l. The reaction is started by adding the enzyme, with the quantity of enzyme being measured such that approx. 50% of the substrate is transformed during the incubation time of 30 min. In order to test the cGMP-stimulatable PDE II, $^3$HcAMP is used as substrate and $10^{-6}$ mol/l unlabeled cGMP is added to the formulation. In order to test the Ca$^{2+}$-calmodulin-dependent PDE I, 1 μM CaCl$_2$ and 0,1 μM calmodulin are additionally added to the reaction formulation. The reaction is stopped by adding 100 μl of acetonitrile which contains 1 mM cAMP and 1 mM AMP. 100 μl of the reaction formulation are separated by HPLC and the cleavage products are determined quantitatively online using a flow-through scintillation counter. The substance concentration at which the reaction rate is decreased by 50% is measured. The "phosphodiesterase [$^3$H] cAMP-SPA enzyme assay" and the "phosphodiesterase [$^3$H] cGMP-SPA enzyme assay", supplied by Amersham Life Science, were additionally used for the testing. The test was carried out using the experimental protocol specified by the manufacturer. The [$^3$H] cAMP-SPA assay was used for determining the activity of PDE II, with $10^{-6}$ M cGMP being added to the reaction formulation for the purpose of activating the enzyme. $10^{-7}$ M calmodulin and 1 μM CaCl$_2$ were added to the reaction formulation for the purpose of measuring PDE I. PDE V was measured using the [$^3$H] cGMP-SPA assay.

In principle, the inhibition of one or more phosphodiesterases of this type leads to an increase in the concentration of cGMP. As a result, the compounds are of interest for all therapies in which an increase in the concentration of cGMP can be assumed to be therapeutic.

The investigation of the cardiovascular effects was carried out on normotensive rats and on SH rats and on dogs. The substances were administered intravenously or orally.

The examination for erection-inducing effect was carried out on conscious rabbits [H. Naganuma, T. Egashira, J. Fuji, Clinical and Experimental Pharmacology and Physiology, 20, 177–183 (1993)]. The substances were administered orally or parenterally.

The novel active compounds, and also their physiologically harmless salts (e.g. hydrochlorides, maleates or lactates), can be converted, in a known manner, into the customary formulations, such as tablets, coated tablets, pills, granules, aerosols, syrups, emulsions, suspensions and solutions, using inert, nontoxic, pharmaceutically suitable carrier substances or solvents. In this connection, the therapeutically effective compound should in each case be present at a concentration of from about 0.5 to 90% by weight of the total mixture, i.e. in quantities which are sufficient for achieving the specified dosage range.

The formulations are prepared, for example, by extending the active compounds with solvents and/or carrier substances, where appropriate using emulsifiers and/or dispersants, with it being possible, for example when using water as diluent, to use organic solvents as auxiliary solvents, where appropriate.

The administration is effected in a customary manner, preferably orally, transdermally or parenterally, for example perlingually, by the buccal route, intravenously, nasally, rectally or by inhalation.

For use in humans, doses of from 0.001 to 50 mg/kg, preferably 0.01 mg/kg–20 mg/kg, are generally administered when administering orally. A dose of 0.001 mg/kg–0.5 mg/kg is expedient when administering parenterally, such as, for example, by way of mucosae, nasally, by the buccal route or by inhalation.

Despite this, it may be necessary, where appropriate, to depart from the mentioned quantities, specifically in dependence on the body weight or the nature of the route of administration, on the individual response to the medicament, on the nature of its formulation and on the time or interval at which the administration takes place. Thus, it can in some cases be sufficient to make do with less than the abovementioned smallest quantity whereas, in other cases, the mentioned upper limit has to be exceeded. When relatively large quantities are being administered, it may be advisable to divide up these quantities into several individual doses which are given during the course of the day.

The compounds according to the invention are also suitable for use in veterinary medicine. For uses in veterinary medicine, the compounds, or their nontoxic salts, can be administered in a suitable formulation, in accordance with common veterinary procedures. The veterinarian can establish the nature of the use, and the dose, in accordance with the nature of the animal to be treated.

Preparing the precursors

EXAMPLE I

Cyclopentanecarbaldehyde

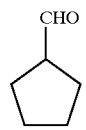

A solution of 128.7 g (1.1 mol) of N-formylpiperidine in 450 ml of diethyl ether is added dropwise, at 0° C., to 669 ml of a 2M solution of cyclopentylmagnesium chloride in diethyl ether (1.1 mol). After the dropwise addition has been completed, the reaction mixture is stirred at room temperature for 1.5 hours. It is poured onto water and this mixture is extracted three times with diethyl ether; the organic phase is washed with sodium hydrogencarbonate solution and dried over sodium sulfate and the solvent is removed in vacuo. This results in 84.4 g of crude product (HPLC purity, 75%), which is subjected to further reaction as such.

EXAMPLE II

1-Cyclopentyl-2-nitro-1-ethanone

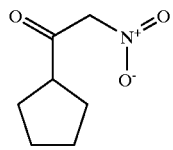

84.36 g (859 mmol) of cyclopentanecarbaldehyde (example I), 262 g (4.29 mol) of nitromethane and 9.99 g (171 mmol) of anhydrous potassium fluoride are stirred overnight, at room temperature, in 900 ml of isopropanol. The mixture is filtered and the solvent is removed in vacuo. 136.28 g (89%) of oil are obtained.

21.67 g (136 mmol) of this oil are dissolved, together with 4.62 g of tetra-n-butylammonium hydrogensulfate, in 200 ml of dichloromethane and the solution is cooled down to −10° C. At the same time, 210 ml of 30% sulfuric acid and 52.06 g (177 mmol) of potassium dichromate are slowly added at this temperature. After 2 hours at −10° C., 180 ml of 10% iron(II) sulfate solution are added, after which the phases are separated and the organic phase is dried over sodium sulfate. Filtration through silica gel yields 14.92 g (62%) of oil. 200 MHz $^1$H-NMR (CDCl$_3$): 1.69, m, 8H; 3.02, quin., 1H; 5.91, s, 2H.

EXAMPLE III

1-Cyclopentyl-2-nitro-1-ethanone oxime

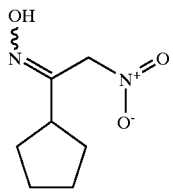

9.90 g (63 mmol) of 1-cyclopentyl-2-nitro-ethanone (example II) and 20.688 g (126 mmol) of hydroxylamine sulfate are heated under reflux, for 4 hours, in 310 ml of a toluene/ethanol mixture (1:1). The solvent is removed in vacuo and the residue is taken up in ethyl acetate; the organic phase is washed 2 times with water and dried over sodium sulfate and the solvent is removed in vacuo. 9.62 g (74%) of pale yellow solid are obtained.

200 MHz $^1$H-NMR (CDCl$_3$): 1.65, m, 6H; 1.93, m, 2H; 2.80, quin., 1H; 5.20, s, 2H; 9.19, s, broad, 1H.

EXAMPLE IV

Ethyl 3-cyclopentyl-4-nitro-isoxazole-5-carboxylate

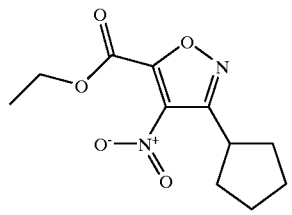

137.2 g (798 mmol) of 1-cyclopentyl-2-nitro-ethanone oxime (example III) and 119.78 g (877 mmol) of ethyl oxalyl chloride are stirred overnight, at room temperature, in 1.4 l of anhydrous ether. The reaction mixture is cooled down to 0° C. and 246 ml of triethylamine are added dropwise. After 2 hours at room temperature, the mixture is diluted with ether and extracted with ammonium chloride solution and water; the organic phase is then dried over sodium sulfate. Chromatographic purification (toluene) yields 51.59 g (82% purity, 20.7%) of yellow oil.

200 MHz $^1$H-NMR (CDCl$_3$): δ=1.44, t, 3H; 1.80, m, 6H; 2.11, m, 2H; 3.44, m, 1H; 4.51, quart., 2H.

EXAMPLE V

3-Cyclopentyl-4-nitro-isoxazole-5-carboxamide

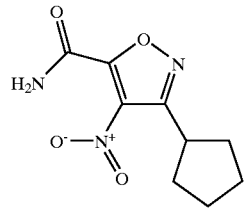

51.59 g (203 mmol) of ethyl 3-cyclopentyl-4-nitro-isoxazole-5-carboxylate (example IV) are stirred, at room temperature for 3 hours, in 600 ml of a 2M solution of ammonia. The solvent is removed in vacuo and the residue is triturated with cyclohexane and dried in vacuo. 31.17 g (62%) of colorless solid are obtained.

200 MHz $^1$H-NMR (CDCl$_3$): δ=1.78, m, 6H; 2.13, m, 2H; 3.52, m, 1H; 7.92,s, broad, 1H; 8.28, s, broad, 1H.

EXAMPLE VI

4-Amino-3-cyclopentyl-isoxazole-5-carboxamide

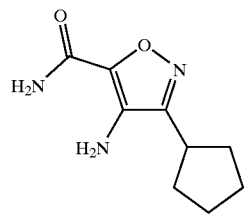

3.15 g (13.9 mmol) of 3-cyclopentyl-4-nitro-isoxazole-5-carboxamide (example V) and 17.51 g (327 mmol) of ammonium chloride are suspended in 70 ml of water and the suspension is cooled to 0° C. 8.5 g (118 mmol) of zinc powder are added in small portions while stirring vigorously. The reaction mixture is stirred at room temperature for 30 minutes. For the working up, filtration takes place through kieselguhr with the kieselguhr subsequently being washed with ethyl acetate, and the filtrate is evaporated to dryness in vacuo. The residue is triturated with ethyl acetate. After filtering, the solvent is removed in vacuo. 1.95 g (70%) of colorless solid are obtained.

200 MHz $^1$H-NMR (CDCl$_3$): δ=1.80, m, 6H; 2.06, m, 2H; 3.07, m, 1H; 4.28, s, broad, 2H; 5.74, s, broad, 1H; 6.02, s, broad, 1H.

EXAMPLE VII

3-Cyclopentyl-4-[(2-ethoxybenzoyl)amino]-isoxazole-5-carboxamide

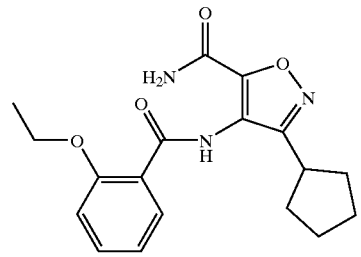

390.5 mg (2.0 mmol) of 4-amino-3-cyclopentyl-isoxazole-5-carboxamide (example VI) are introduced, together with a catalytic quantity of 4-N,N- dimethylaminopyridine (DMAP), into 2.0 ml of pyridine. 553.9 mg (3.0 mmol) of 2-ethoxybenzoyl chloride are added and the mixture is subsequently stirred at 60° C. for 5 h before a further 277 mg of 2-ethoxybenzoyl chloride are added. After an additional 5 h at 60° C., the reaction mixture is taken up in dichloromethane and this solution is washed twice with saturated sodium hydrogencarbonate solution. The organic phase is dried over magnesium sulfate and concentrated on a rotary evaporator, and the residue is dried under high vacuum. Purification takes place by means of flash chromatography using dichloromethane/methanol 95:5.

Yield: 168 mg (21% of theory)

$R_f$ value=0.368, dichloromethane/methanol 95:5

MS (DCI, NH$_3$): m/z (%)=344 (M+H) (100)

$^1$H-NMR (200 MHz, CDCl$_3$): δ=1.61 (t, 3H); 1.62–1.89 (m, 6H); 2.03–2.17 (m, 2

H); 3.54 (qui, 1H); 4.35 (q, 2H); 5.74 (bs, 1H); 6.48 (bs, 1H); 7.02–7.15 (m, 2H);

7.52 (dt, 1H); 8.27 (dd, 1H); 10.30 (bs, 1H).

EXAMPLE VIII

3-Cyclopentyl-5-(2-ethoxyphenyl)-isoxazolo[4,5-d]pyrimidin-7(6H)-one

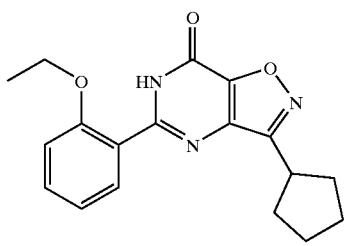

1.7 g (4.95 mmol) of 3-cyclopentyl-4-[(2-ethoxybenzoyl)amino]-isoxazole-5-carboxamide (example VII) are introduced into 30 ml of toluene. 1.55 g (7.4 mmol) of phosphorus oxychloride are added to the suspension and the mixture is subsequently stirred under reflux for 2 h. It is then diluted with ethyl acetate and washed with 1N sodium hydroxide solution. The organic phase is dried and concentrated on a rotary evaporator. The product is isolated from the mixture by chromatography on silica gel using cyclohexane/ethyl acetate 6:4.

Yield: 79.2 mg (4.9% of theory)

MS (DCI, NH$_3$): m/z (%)=343 (M+18) (100), 326 (M+H) (58), 242 (34)

$^1$H-NMR (200 MHz, CDCl$_3$): δ=1.67 (t, 3H); 1.70–2.30 (m, 8H); 3.52 (qui, 1H);

4.32 (q, 2H); 7.02–7.21 (m, 2H); 7.52 (dt, 1H); 8.49 (dd, 1H); 11.68 (bs, 1H).

EXAMPLE IX 3-(3-Cyclopentyl-7-oxo-6,7-dihydroisoxazolo[4,5-d]pyrimidin-5-yl)-4-ethoxy-benzenesulfonyl chloride

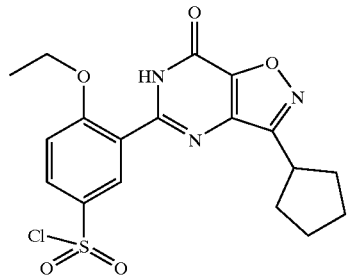

0.24 ml (3.6 mmol) of chlorosulfonic acid is introduced while cooling with ice. 130 mg (0.4 mmol) of 3-cyclopentyl-5-(2-ethoxyphenyl)-isoxazolo[4,5-d]pyrimidin-7(6H)-one (example VIII) are added in portions and the mixture is subsequently stirred overnight under reflux; after that, it is diluted with dichloromethane and poured onto ice water. The organic phase is separated off and extraction with dichloromethane takes place again; the organic phases are combined, dried and evaporated.

Yield: 134 mg (81.8% of theory)

$^1$H-NMR (200 MHz, CDCl$_3$): δ=1.70 (t, 3H); 1.65–2.35 (m, 8H); 3.58 (m, 1H);

4.49 (q, 2H); 7.28 (d, 1H); 8.18 (dd, 1H); 9.13 (d, 1H); 11.33 (bs, 1H).

EXAMPLE X

3-Cyclopentyl-4-{[2-(4-methoxyphenyl)acetyl]amino}-isoxazole-5-carboxamide

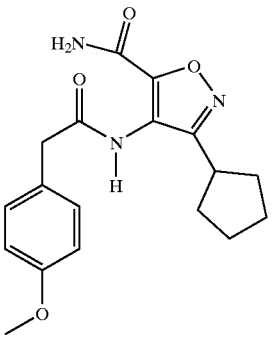

12 g (61 mmol) of 4-amino-3-cyclopentyl-isoxazole-5-carboxamide (example VI) are dissolved in 50 ml of pyridine, and 12.48 g (67 mmol) of 4-methoxyphenylacetyl chloride and a spatula tip of DMAP are added. The reaction mixture is stirred at 60° C. for 5 hours and the solvent is then removed in vacuo. The residue is taken up in dichloromethane and the solution is shaken twice with 1N hydrochloric acid and twice with sodium hydrogencarbonate solution; it is then dried over sodium sulfate and the solvent is removed in vacuo. The residue is triturated with a little dichloromethane and then filtered; the filtrate is concentrated to dryness and the residue is purified by chromatography (cyclohexane/ethyl acetate=2:1).

Yield: 2.56 g

200 MHz $^1$H-NMR (DMSO-D$_6$): 1.55, m, 8H; 2.92, m, 1H; 3.56, s, 2H; 3.72, s, 3H;

6.88, d, 2H; 7.27, d, 2H; 7.92, s, broad, 1H; 8.08, s, broad, 1H; 9.76, s, 1H.

EXAMPLE XI

3-Cyclopentyl-5-(4-methoxyphenyl)-isoxazolo[4,5-d]pyrimidin-7(6H)-one

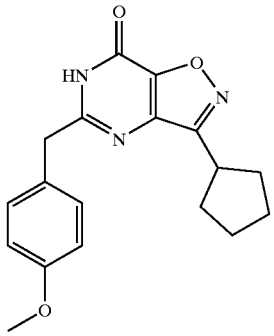

2.56 g (7.45 mmol) of 3-cyclopentyl-4-{[2-(4-methoxyphenyl)acetyl]amino}-isoxazole-5-carboxamide (example X) are heated under reflux for 16 hours, together with 4.3 g of potassium hydroxide, in 170 ml of methanol. The solvent is removed in vacuo and the residue is taken up in dichloromethane; the solution is washed with 1N hydrochloric acid and water, after which the organic phase is dried over sodium sulfate and the solvent is removed. The residue is purified by chromatography (cyclohexane/ethyl acetate= 2:1).

Yield: 0.93 g (38% of theory)

200 MHz $^1$H-NMR (DMSO-D$_6$): 1.73, m, 6H; 2.08, m, 2H; 3.38, m, 1H; 3.71, s, 3H;

3.91, s, 2H; 6.89, d, 2H; 7.27, d, 2H; 13.06, s, broad, 1H.

EXAMPLE XII

5-[(3-Cyclopentyl-7-oxo-6,7-dihydroisoxazolo[4,5-d]pyrimidin-5-yl)methyl]-2-methoxybenzen chloride

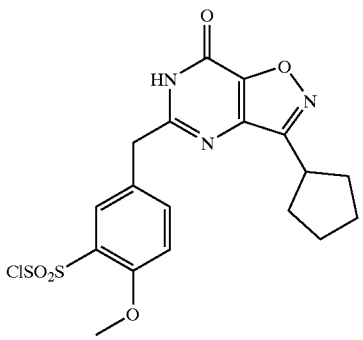

1.23 g (3.78 mmol) of 3-cyclopentyl-5-(4-methoxybenzyl)-isoxazolo[4,5-d]-pyrimidin-7(6H)-one (example XI) are introduced in portions into 2.51 ml of chlorosulfonic acid at 0° C. The reaction mixture is stirred at room temperature for 16 hours. It is poured onto ice water and the precipitate is filtered off with suction and dried in vacuo.

Yield: 1.31 g (77% of theory)

200 MHz $^1$H-NMR (CDCl$_3$): 1.78, m, 6H; 2.19, m, 2H; 3.48, quin., 1H; 4.03, s, 3H;

4.15, s, 2H; 7.11, d, 1H; 7.81, dd, 1H; 8.06, d, 1H; 12.52, s, broad, 1H.

Preparing the Active Compounds

EXAMPLE 1

3-Cyclopentyl-5-(2-ethoxy-5-{[4-(2-hydroxyethyl)piperazino]sulfonyl}phenyl)-isoxazolo[4,5-d]pyrimidin-7(6H)-one

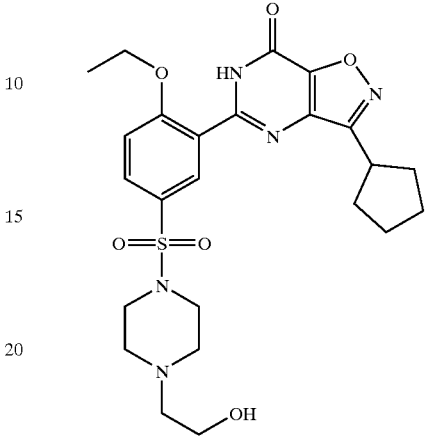

130 mg (0.31 mmol) of the sulfonyl chloride from example IX are introduced into 7 ml of dichloromethane. 120 mg (0.92 mmol) of N-hydroxyethylpiperazine are added and the mixture is subsequently stirred overnight at room temperature. It is then diluted with dichloroethane, washing is carried out with water, extraction is carried out again with dichloroethane, drying is carried out and evaporation is carried out. The resulting residue is crystallized with ether and the product is filtered off with suction.

Yield: 129 mg (81.3% of theory)

R$_f$ value=0.253, dichloromethane/methanol 95:5

MS (DCI, NH$_3$): m/z (%)=518 (M+H) (100)

$^1$H-NMR (200 MHz, CDCl$_3$): δ=1.69 (t, 3H); 1.70–2.31 (m, 9H); 2.54–2.68 (m, 6 H); 3.06–3.15 (m, 4H); 3.48–3.62 (m, 3H); 4.45 (q, 2H); 7.22 (d, 1H); 7.90 (dd, 1 H); 8.84 (d, 1H).

EXAMPLE 2

3-(3-Cyclopentyl-7-oxo-6,7-dihydroisoxazolo[4,5-d]pyrimidin-5-yl)-N-(3,4-dimethoxyphenethyl)-4-ethoxy-N-methyl-benzenesulfonamide

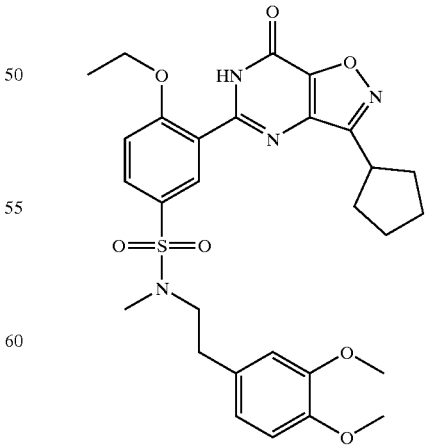

89.8 mg (0.46 mmol) of N-methylhomoveratrylamine are added to a solution of 65 mg (0.153 mmol) of the sulfonyl chloride from example IX in 5 ml of dichloromethane. The mixture is stirred overnight at room temperature before the crude product, after concentrating the mixture, is purified by means of preparative TLC chromatography using dichloromethane/methanol 95:5. The oily residue is crystallized with ether.

Yield: 88 mg (98.5% of theory)

MS (ESI-pos.): m/z (%)=605 (M+Na) (100), 583 (M+H) (66)

$^1$H-NMR (200 MHz, CDCl$_3$): δ=1.59 (t, 1H); 1.62–2.23 (m, 8H); 2.80 (s, 3H);

2.80–2.88 (m, 2H); 3.29 (bt, 2H); 3.51 (qui, 1H); 3.85 (s, 6H); 4.25 (q, 2H); 6.68–6.78 (m, 2H); 7.11 (d, 2H); 7.82 (dd, 1H); 8.71 (d, 1H).

EXAMPLE 3

3-Cyclopentyl-5-{4-methoxy-3-[(4-methylpiperazino)sulfonyl]benzyl}-isoxazolo[4,5-d]pyrimidin-7(6H)-one

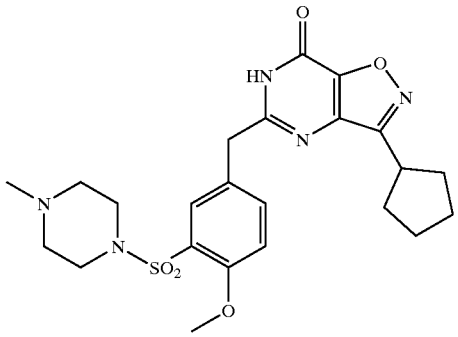

40 mg (0.08 mmol) of the sulfonyl chloride from example IX are dissolved in 1 ml of dichloromethane, and 20 mg (0.24 mmol) of N-methylpiperazine and a spatula tip of DMAP are added at 0° C. The reaction mixture is stirred at room temperature for 16 hours. After diluting with dichloromethane, the mixture is extracted with ammonium chloride solution and dried over sodium sulfate and the solvent is removed in vacuo. The residue is purified by chromatography (dichloromethane/methanol 30:1).

Yield: 30 mg (75% of theory)

200 MHz $^1$H-NMR (CDCl$_3$): 1.84, m, 6H; 2.15, m, 2H; 2.29, s, 3H; 2.43, m, 4H;

3.21, m, 4H; 3.49, m, 1H; 3.88, s, 3H; 4.05, s, 2H; 6.92, d, 1H; 7.54, dd, 1H; 7.91, d, 1H.

EXAMPLE 4

3-Cyclopentyl-5-{3-[(4-hydroxypiperidino)sulfonyl]-4-methoxyphenyl}-isoxazolo-[4,5-d]pyrimidin-7(6H)-one

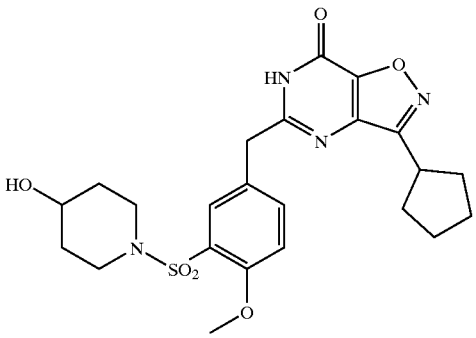

The preparation is effected by analogy with example 3, proceeding from 40 mg (0.08 mmol) of the sulfonyl chloride from example IX and 30 mg (0.24 mmol) of 4-hydroxypiperidine.

Yield: 14 mg (33% of theory)

200 MHz $^1$H-NMR (CDCl$_3$): 1.59, m, 2H; 1.89, m, 8H; 2.15, m, 2H; 3.02, m, 2H;

3.48, m, 1H; 3.81, m, 1H; 3.89, s, 3H; 4.08, s, 2H; 6.98, d, 1H; 7.55, dd, 1H; 7.91, d, 1H.

EXAMPLE 5

5-[(3-Cyclopentyl-7-oxo-6,7-dihydroisoxazolo[4,5-d]pyrimidin-5-yl)methyl]-2-methoxy-N-(4-pyrimidyl)benzenesulfonamide

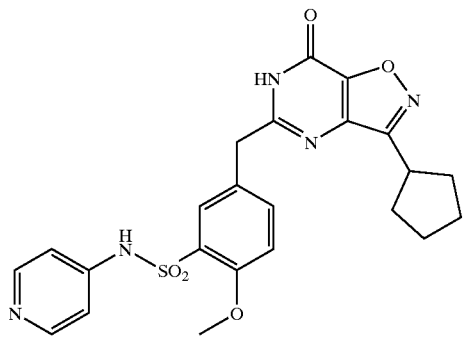

The preparation is effected by analogy with example 3, proceeding from 40 mg (0.08 mmol) of the sulfonyl chloride from example XII and 20 mg (0.24 mmol) of 4-aminopyridine.

Yield: 5 mg (11%)

R$_f$ value=0.12 (dichloromethane/methanol=10:1)

EXAMPLE 6

5-[(3-Cyclopentyl-7-oxo-6,7-dihydroisoxazolo[4,5-d]pyrimidin-5-yl)methyl]-N-(3-fluoro-4-methoxyphenyl)-2-methoxybenzenesulfonamide

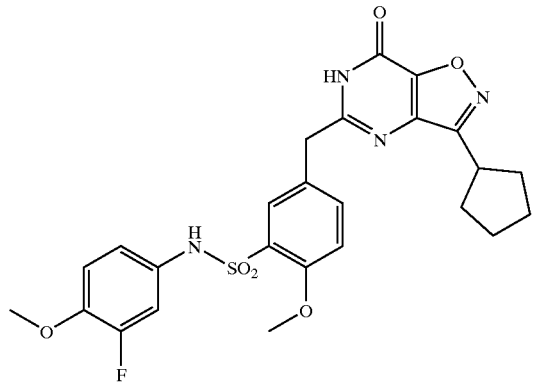

The preparation is effected by analogy with example 3, proceeding from 40 mg (0.08 mmol)) of the sulfonyl chloride from example XII and 30 mg (0.24 mmol) of 4-methoxy-3-fluoroaniline Yield: 2 mg (4%)

R$_f$ value=0.41 (cyclohexane/ethyl acetate=1:2)

What is claimed is:

1. An isoxazolopyrimidinone of formula (I)

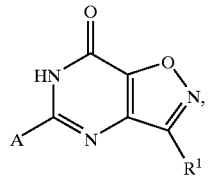

in which

R$^1$ represents (C$_3$–C$_8$)-cycloalkyl or represents straight-chain or branched alkyl having up to 4 carbon atoms, A represents radicals of the formulae

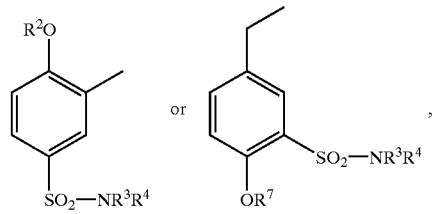

in which

R$^2$ and R$^7$ are identical or different and represent hydrogen or straight-chain or branched alkyl having up to 4 carbon atoms, R$^3$, R$^4$, R$^5$ and R$^6$ are identical or different and represent hydrogen, a 5- to 6-membered aromatic heterocycle selected from the group consisting of pyridyl, pyrimidyl, pyridazinyl, thienyl, furyl, pyrrolyl, thiazolyl, oxazolyl or imidazolyl, or aryl having 6 to 10 carbon atoms, where the ring systems are optionally substituted, up to three times, identically or differently, by hydroxyl, halogen, (C$_1$–C$_5$)-alkyl or (C$_1$–C$_6$)-alkoxy, or R$^3$, R$^4$, R$^5$ and R$^6$ are identical or different and represent (C$_1$–C$_6$)-alkyl which is optionally substituted by aryl having from 6 to 10 carbon atoms and can, for its part, be substituted, up to 3 times, identically or differently, by (C$_1$–C$_6$)-alkyl, (C$_1$–C$_6$)-alkoxy, hydroxyl or halogen, or R$^3$ and R$^4$ and/or R$^5$ and R$^6$, together with the nitrogen atom to which they are bonded, form radicals of the formulae

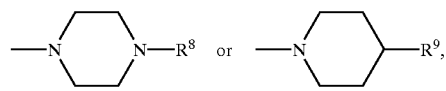

where

R$^8$ represents hydrogen or (C$_1$–C$_6$)-alkyl which is optionally substituted by hydroxyl, and R$^9$ represents hydrogen or hydroxyl, and the salts, N-oxides and isomeric forms thereof.

2. The isoxazolopyrimidinone of formula (I) as claimed in claim 1, in which

R$^1$ represents (C$_3$–C$_6$)-cycloalkyl or represents n-propyl,

A represents radicals of the formulae

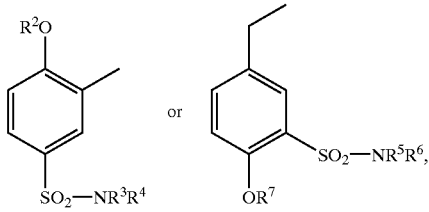

in which

R$^2$ and R$^7$ are identical or different and represent hydrogen, methyl or ethyl, R$^3$, R$^4$, R$^5$ and R$^6$ are identical or different and represent hydrogen, pyridyl, pyrimidyl, pyridazinyl, furyl, imidazolyl, thienyl, pyrryl or phenyl, where the ring systems are optionally substituted, up to 2 times, identically or differently, by hydroxyl, fluorine, chlorine, (C$_1$–C$_4$)-alkyl or (C$_1$–C$_4$)-alkoxy, or R$^3$, R$^4$, R$^5$ and R$^6$ are identical or different and represent (C$_1$–C$_4$)-alkyl which is optionally substituted by phenyl which, for its part, can be substituted, up to 2 times, identically or differently, by (C$_1$–C$_4$)-alkoxy, fluorine or chlorine, or R$^3$ and R$^4$ and/or R$^5$ and R$^6$, together with the nitrogen atom to which they are bonded, form radicals of the formulae

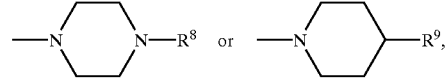

where

R$^8$ represents hydrogen or (C$_1$–C$_6$)-alkyl which is optionally substituted by hydroxyl, and R$^9$ represents hydroxyl, and the salts, N-oxides and isomeric forms thereof.

3. The isoxazolopyrimidinone of formula (I) as claimed in claim 1, in which

R$^1$ represents cyclopentyl or n-propyl,

A represents radicals of the formulae

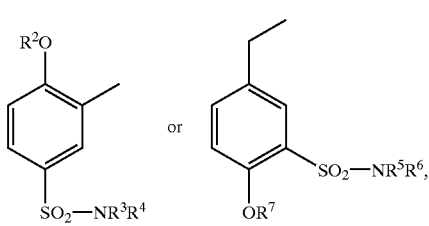

in which

R$^2$ and R$^7$ are identical or different and represent methyl or ethyl,

R$^3$, R$^4$, R$^5$ and R$^6$ are identical or different and represent hydrogen, pyridyl or phenyl, where the ring systems are optionally substituted, up to 2 times, identically or differently, by fluorine, methoxy or ethoxy, or $R^3$, $R^4$, $R^5$ and $R^6$ are identical or different and represent ($C_1$–$C_3$)-alkyl which is optionally substituted by phenyl which, for its part, is substituted, up to 2 times, identically or differently, by methoxy or ethoxy, or $R^3$ and $R^4$ and/or $R^5$ and $R^6$, together with the nitrogen atom to which they are bonded, form radicals of the formulae

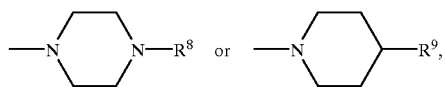

where $R^8$ represents hydrogen or ($C_1$–$C_3$)-alkyl or a radical of the formula —$(CH_2)_2$—OH, and $R^9$ represents hydroxyl, and the salts, N-oxides and isomeric forms thereof.

4. The isoxazolopyrimidinone of formula (I) as claimed in claim 1 and having one of the following structures:

| Structure |
| --- |
| 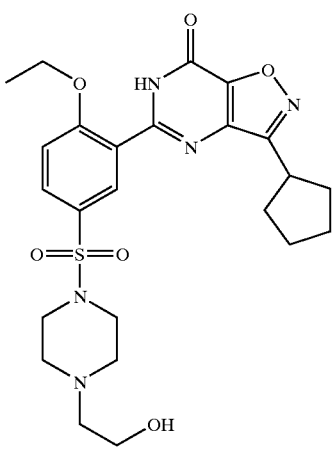 |
| 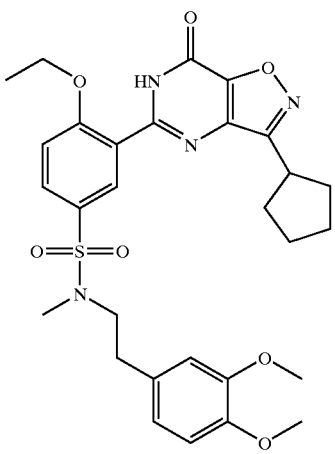 |
| 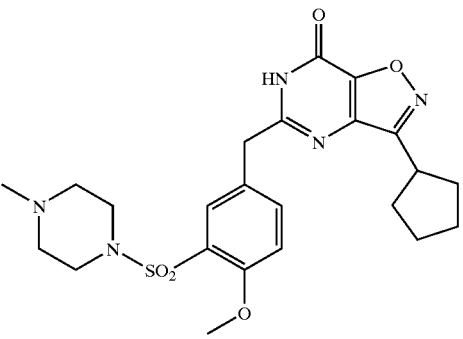 |

5. A process for preparing isoxazolopyrimidinones as claimed in claim 1, characterized in that compounds of formula (II)

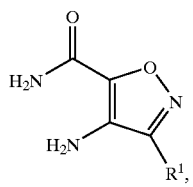

(II)

in which $R^1$ has the meaning indicated in claim 1, are initially converted, by reaction with compounds of the general formula (III)

A'—CO—Cl  (III), in which

A' represents radicals of the formulae

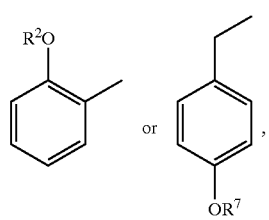

in which $R^2$ and $R^7$ have the meaning indicated in claim 1, in inert solvents, where appropriate in the presence of a base, into the compounds of formula (IV)

(IV)

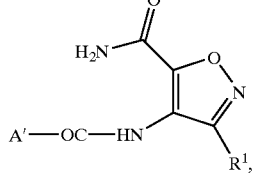

in which

A' has the abovementioned meaning and $R^1$ has the meaning indicated in claim 1, a cyclization is subsequently carried out, in the presence of POCl$_3$ or of alkali metal hydroxide or alkaline earth metal hydroxide, to give the compounds of formula (V)

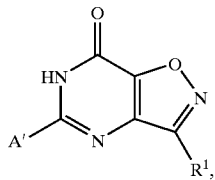
(V)

in which

A' has the abovementioned meaning and R$^1$ has the meaning indicated in claim 1, and, in a further step, the compounds of formula (VI)

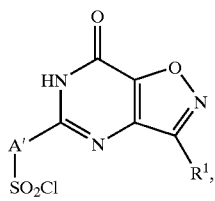
(VI)

in which

A' has the abovementioned meaning and R$^1$ has the meaning indicated in claim 1, are prepared by reaction with ClSO$_3$H, and, finally, are reacted with amines of formula (VII)

HNR$^{10}$R$^{11}$ (VII), in which

R$^{10}$ and R$^{11}$ encompass the scope of meaning of R$^3$, R$^4$, R$^5$ and R$^6$ as indicated in claim 1.

6. A pharmaceutical composition comprising one or more compounds of formula (I) as claimed in any one of claims 1 to 4 and one or more pharmacologically harmless auxiliary substances and carrier substances.

7. A method for the treatment of diseases of the urogenital system comprising administering to a subject in need thereof an effective amount of a compound of the Formula (I) as claimed in one of claims 1 to 4.

8. The method of claim 7 wherein said diseases of the urogenital system are selected from the group consisting of prostate hypertrophy, incontinence, erectile dysfunction and female sexual dysfunction.

9. The method as claimed in claim 7 or 8, characterized in that the compositions are administered intravenously or orally.

\* \* \* \* \*